US005932195A

United States Patent [19]

Drögemüller et al.

[11] Patent Number: 5,932,195

[45] Date of Patent: Aug. 3, 1999

[54] ARYLAMINOMETHYLENECAMPHOR DERIVATIVES

[75] Inventors: Michael Drögemüller, Mannheim; Volker Bomm, Mutterstadt; Volker Schehlmann, Römerberg; Horst Westenfelder, Neustadt, all of Germany

[73] Assignee: BASF Aktiengesellschaft, Ludwigshafen, Germany

[21] Appl. No.: 09/006,175

[22] Filed: Jan. 13, 1998

[30] Foreign Application Priority Data

Jan. 17, 1997 [DE] Germany ........................... 197 01 448

[51] Int. Cl.[6] .............................. A61K 7/42; A61K 7/44; C07C 225/14; C07C 229/56

[52] U.S. Cl. .............................. 424/60; 424/59; 514/535; 514/646; 514/657; 514/313; 514/603; 514/559; 546/159; 560/19; 562/46; 562/58; 562/457; 564/86; 564/305

[58] Field of Search ........................ 424/59, 60; 564/305; 560/19; 514/646, 657, 535; 562/46, 58, 457

[56] References Cited

U.S. PATENT DOCUMENTS

| | | | |
|---|---|---|---|
| 4,663,155 | 5/1987 | Murray et al. | 424/59 |
| 4,766,235 | 8/1988 | Lang et al. | 560/51 |
| 5,639,883 | 6/1997 | Poetsch et al. | 546/137 |

FOREIGN PATENT DOCUMENTS

| | | |
|---|---|---|
| 2336219 | 7/1973 | Germany . |
| 4426216 | 7/1994 | Germany . |

OTHER PUBLICATIONS

Knorr R & Ruf F. Chem. Ber. 118(11), 4486–95, 1985.

Terent'ev AP et al. Zh. Obshch. Khim. 40(6), 1398–404, 1970.

Gogte VN et al. Indian J. Chem., Sect. B. 15B (9), 778–81, 1977.

Kupletskaya NB et al. Zh. Fiz. Khim. 45(6), 1429–33, 1971.

Vankar YD et al. Indian J. Chem., Sect. B. 15B (5), 411–15, 1977.

Singh et al., *J. Ind. Chem. Soc.*, vol. 17, 1940, pp. 1–18.

Rupe et al., *Helv. Chem. Acta III*, 1920, pp. 71–89.

*Chem. Abst.*, vol. 32, No. 10, 1932, col. 3763.

Knorr et al., *Chem. Berich.*, 1985, vol. 118, No. 11, pp. 4486–4495.

*Chem. Abst.*, vol. 74, No. 7, 1971, AN 31852.

*Chem. Abst.*, vol. 14, No. 11, 1920, pp. 1665.

Singh et al., *J. Ind. Chem. Soc.*, XX, 1943, pp. 1–10.

Gogte et al., *Ind. J. Chem.*, vol. 15B, 1977, pp. 778–781.

Lowe et al., *Sunscreens*, (1990), pp. 230–231.

Claisen, Ann., der Cheurie pp. 306–313, (1894).

*Primary Examiner*—Evelyn Mei Huang

*Attorney, Agent, or Firm*—Keil & Weinkauf

[57] ABSTRACT

Arylaminomethylenecamphor derivatives of the formula (1)

(1)

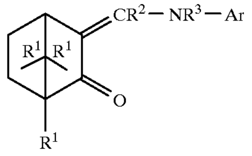

where the C═C double bond is in the Z or E configuration, and the variables have the following meanings:

$R^1$ H, $CH_3$, $R^2$ H, $C_1$–$C_6$-alkyl, $C_3$–$C_8$-cycloalkyl, $C_2$–$C_6$-alkenyl, $C_3$–$C_8$-cycloalkenyl, aryl or substituted aryl, $R^3$ H, $C_1$–$C_6$-alkyl, $C_3$–$C_8$-cycloalkyl, aryl, substituted aryl, $C_1$–$C_6$-alkoxy, $C_1$–$C_8$-acyl, Ar aryl, substituted aryl, hetaryl or substituted hetaryl, are used as sunscreen agents, especially in cosmetic and pharmaceutical formulations.

7 Claims, No Drawings

ARYLAMINOMETHYLENECAMPHOR DERIVATIVES

The present invention relates to arylaminomethylenecamphor derivatives of the formula (1), (1)

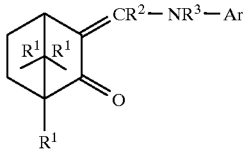

and to their use as sunscreen agents, especially in cosmetic and pharmaceutical formulations.

Sunscreen filters based on camphor derivatives are known. DE 23 36 219 describes sulfonated benzylidene- and cinnamylidenecamphor derivatives which are unsubstituted or substituted in position 4 of the phenyl ring by methyl, methoxy or chlorine.

DE 34 45 712 describes a number of unsaturated camphor derivatives, preferably benzylidenecamphor derivatives, which are suitable as drugs for treating skin disorders.

DE 44 26 216 describes benzylidenenorcamphor derivatives which can be employed as sun filters and for preventing inflammations and skin disorders.

DE 44 24 489 describes a process for preparing substituted 4-methylidenecinnamic acid derivatives.

Sunscreen filters based on vinylogous amides are likewise known. DE 33 16 287 describes a number of vinylogous amides which have an open-chain structure and are suitable as light filters in sunscreen compositions.

The requirements to be met by a sunscreen agent intended to be employed as UV-A filter are numerous (Sunscreens, ed. N. J. Lowe, N. A. Shaath, Marcel Dekker Inc., New York 1990, 230–231). The most important are:

1) It has its absorption maximum in the UV-A region from 320 to 360 nm;
2) it has a high specific absorption in this region;
3) it is colorless, ie. the absorption above 400 nm should be vanishingly small in order to preclude coloring of the skin-protecting product or the clothing after use;
4) it is photo- and thermostable;
5) it is compatible with skin and causes no irritant or toxic effects on the skin;
6) it adheres well to the skin;
7) it is compatible with cosmetic substances and readily soluble in cosmetic solvents and compositions;
8) it is isomerically pure.

The known cinnamylidenecamphor derivatives are broadband UV filters which have an inadequate protective effect in the UV-A region. Furthermore, their solubility, specifically in the oil phase, is unsatisfactory for some applications.

It is an object of the present invention to provide a compound suitable as UV-A filter and having in particular good photostability, good solubility in the oil phase and a pronounced absorption maximum in the UV-A region.

We have found that this object is achieved by arylaminomethylidenecamphor compounds of the formula (1), (1)

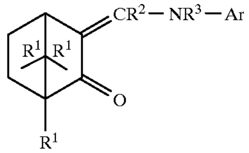

where the C=C double bond is in the Z or E configuration, and $R^1$=H, $CH_3$, $R^2$=H, $C_1$–$C_6$-alkyl, $C_3$–$C_8$-cycloalkyl, $C_2$–$C_6$-alkenyl, $C_3$–$C_8$-cycloalkenyl, aryl or substituted aryl, $R^3$=H, $C_1$–$C_6$-alkyl, $C_3$–$C_8$-cycloalkyl, aryl, substituted aryl, $C_1$–$C_6$-alkoxy, $C_1$–$C_8$-acyl, Ar=aryl, substituted aryl, hetaryl, substituted hetaryl, in an excellent manner.

(1) is prepared by reacting hydroxymethylenecamphor compounds of the formula (2) (prepared as described by L. Claisen, Ann. 281, 1894, 306) with amines of the formula (3) in the presence of a base or an acid, with or without the addition of one or more solvents, at from 0° C. to 200° C.

(2)

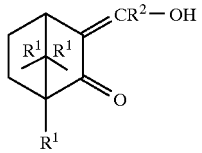

(3)

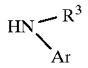

(2) and (3) are reacted in equimolar amounts to prepare a compound according to the invention.

The reaction is generally carried out in protic solvents, eg. methanol or ethanol. However, it can also be carried out in ethers, eg. diethyl ether or tetrahydrofuran, in $C_1$-$C_{20}$ paraffin mixtures or in other aliphatic or aromatic solvents such as hexane, toluene or xylene.

However, it is also possible for the reaction to be carried out without solvent. It is preferably carried out in lower alcohols and, to obtain a good space-time yield, using only sufficient solvent to produce a mixture which is stirrable at the reaction temperature.

(2) and (3) can be reacted in any sequence. The catalyst can be initially present or else metered in. The reaction can also be carried out as a one-pot reaction. It is likewise possible for (2) to be introduced first together with the catalyst, and for (3) to be metered in, and vice versa. It is also conceivable to introduce the catalyst first together with (3) and to meter in (2).

The reaction can be carried out at a temperature in the range from 0° C. to +200° C. The preferred temperature range is from 20° C. to 100° C. The temperature range from 60° C. to 90° C. is particularly preferred.

The reaction time depends directly on the temperature. In general, the reaction is complete after from 1 to 5 hours in the particularly preferred temperature range. At lower temperatures or lower steady state concentrations, the reaction time may increase considerably and take up to 48 h.

Catalysts which can be used are any organic or inorganic bases or else mixtures thereof. Examples of typical basic catalysts are pyridine, trimethylamine or inorganic carbonates. The bases can be present homogeneously or else heterogeneously in the reaction mixture.

The catalysts preferably used for the reaction are organic or inorganic acids or else mixtures thereof. Inorganic acids which can be used are, inter alia, hydrochloric acid, sulfuric acid, nitric acid and/or phosphoric acid.

Organic acids which can be employed are, inter alia, formic acid, acetic acid, oxalic acid, succinic acid, ascorbic acid and/or sulfonic acids such as methanesulfonic acid or toluenesulfonic acid.

In addition, acidic ion exchangers are likewise suitable as catalysts for the reaction of (2) with (3).

The required product (1) is isolated by conventional techniques such as sedimentation, filtration, centrifugation, phase separation and solvent extraction.

The required product (1) can be purified by recrystallization from organic solvents and mixtures thereof and/or water. Mixtures containing alcohols are preferred.

Purification can also take place by zone melting and chromatographic methods, as well as by distillation.

The compounds (1) according to the invention may comprise a camphor moiety ($R^1$=$CH_3$) or a norcamphor moiety ($R^1$=H).

$R^2$ has the following meaning:

H; $C_1$–$C_6$-alkyl, preferably $C_3$- and $C_4$-alkyl such as n-propyl, isopropyl, n-butyl, isobutyl, tert-butyl; $C_3$–$C_8$-cycloalkyl, preferably cyclopropyl, cyclobutyl, cyclopentyl, cyclohexyl; $C_2$–$C_6$-alkenyl, preferably vinyl and propenyl; $C_3$–$C_8$-cycloalkenyl, preferably cyclopentenyl and cyclohexenyl; aryl or substituted aryl, preferably phenyl, mono- or disubstituted phenyl, naphthyl or hetaryl such as furyl, thienyl or pyridyl.

$R^3$ has the following meaning:

H; $C_l$–$C_6$-alkyl, preferably $C_1$–$C_4$-alkyl such as methyl, ethyl, n-propyl, isopropyl, n-butyl, isobutyl, tert-butyl; $C_3$–$C_8$-cycloalkyl, preferably cyclopropyl, cyclobutyl, cyclopentyl, cyclohexyl; aryl or substituted aryl, preferably phenyl, mono- or disubstituted phenyl; $C_1$–$C_6$-alkoxy, preferably methoxy, ethoxy, n-propoxy or isopropoxy; $C_1$–$C_8$-acyl, preferably formyl, acetyl, propionyl, pivaloyl, n-butyryl, isobutyryl, benzoyl.

Ar has the following meaning:

aryl, preferably phenyl, naphthyl; hetaryl, preferably furyl, thienyl, pyrryl or pyridyl; substituted aryl, preferably mono- or disubstituted phenyl; substituted hetaryl, preferably mono- or disubstituted furyl, thienyl, pyrryl or pyridyl, where the substituents can be identical or different and have the following meanings: alkyl, cycloalkyl, alkoxy, amino, alkylamino, hydroxyl, halogen, acyl, particularly preferably acyloxy or acylamino, and alkoxycarbonyl or aminocarbonyl, carboxyl, sulfo or aminosulfonyl.

The C=C double bond in the arylaminomethylenecamphor derivatives (1) according to the invention is present in both the E and the Z configuration after the synthesis. Crystallization results preferentially in compounds of the formula (1) in which the substituents on the C=C double bond are in the trans position.

The compounds (1) according to the invention are distinguished by high photostability and are particularly suitable as sunscreen agents, especially as UV-A filters, in particular for cosmetic and pharmaceutical applications. The UV filter effect can, however, also be used for stabilizing plastics, dye formulations or surface coatings.

Cosmetic products or compositions contain the compounds (1) generally in amounts from 0.1 to 15%, preferably 5–10%, of the weight of the formulation, in addition to excipients and diluents customary in cosmetics, with or without conventional cosmetic auxiliaries.

The nature of the carrier, auxiliary or diluent determines whether the finished sunscreen product is a solution, an oil, a cream, an ointment, a lotion, a gel or a powder. Compositions of these types are to be found, for example, in the journal Seifen, Öle, Fette, Wachse (1955), 147.

Cosmetic auxiliaries which are conventionally used and are suitable as additives are, for example, emulsifiers such as fatty alcohol ethoxylates, sorbitan fatty acid esters or lanolin derivatives, thickeners such as carboxymethylcellulose or crosslinked polyacrylic acid, preservatives and perfumes.

Sunscreen oils are based, for example, on vegetable oils such as arachis oil, olive oil, sesame oil, cottonseed oil, coconut oil, grapeseed oil, castor oil or mineral oils such as liquid petrolatum or, in particular, liquid paraffin, synthetic fatty acid esters and glycerides. Examples of ointment bases are petrolatum, lanolin, eucerin or polyethylene glycols.

Examples of cream bases are high-fat creams, glycerol, polysaccharide and Tylose creams, and of creams based on fats and waxes cetyl alcohol, lanolin cream, cocoa butter, beeswax, stearic acid, stearyl alcohol, glycerol monostearate, natural or mineral oils and fats.

Examples of emulsion bases are mixtures of stearyl glycol, a vegetable and/or mineral oil such as almond oil, liquid paraffin and petrolatum, and water or mixtures of ethyl alcohol, water, lanolin and tragacanth, or mixtures of ethyl alcohol, stearin, water, tragacanth and glycerol or mixtures of stearic acid, liquid paraffin, propyl or isopropyl alcohol and water.

The compounds according to the invention can be employed as the only UV absorber in the appropriate compositions; however, they can also be employed in combination with other UV absorbers, especially UV-B absorbers.

Examples of such compounds are ethyl p-aminobenzoate, 2-ethylhexyl p-methoxycinnamate, 2-ethylhexyl 2-cyano-3,3-diphenylacrylate, 2-phenylbenzimidazolesulfonic acid and salts, 2-hydroxy-4-methoxybenzophenone, 2-hydroxy-4-methoxybenzophenone-5-sulfonic acid, 3-(4-methylbenzylidene)-d,1-camphor, 2,4,6-tris(p-2-ethylhexoxycarbonylanilino)-1,3,5-triazine.

The following general method is particularly preferably used to prepare the compounds (1) according to the invention:

Equimolar amounts (22 mmol) of the hydroxymethylenecamphor compound (2) and of the amine (3) are dissolved in 20 ml of methanol and, after addition of 0.1 ml of concentrated hydrochloric acid, heated at 65° C. for 2 h. After the reaction mixture has been cooled to 10° C., the required product (1) crystallizes out and can be isolated analytically pure by filtration, washing and subsequent drying.

EXAMPLE 1

4 g (22 mmol) of hydroxymethylenecamphor were reacted with 5.45 g (22 mmol) of 2-ethylhexyl p-aminobenzoate by the general method to result in 9 g of a compound of the formula:

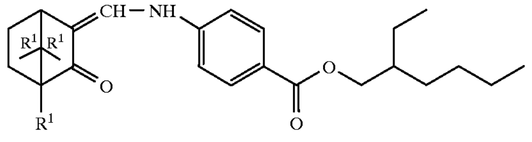

$R^1 = CH_3$

UV($CH_3OH$): $\lambda_{max}$ =358 nM, $E_1^1$=1044

IR: v=3220, 2959, 1711, 1692, 1636, 1602 (s), 1587, 1263 (s), 1176, 1105, 1072 $cm^{-1}$.

HH-NMR ($CDCl_3$): δ=9.87 (d, 1H, J=11.2 Hz), 7.95 (d, 2H, J=7.6 Hz), 6.91 (m, 3H), 4.16 (d, 2H, J=8.2 Hz), 5 2.40 (m, 1H), 2.01 (m, 1H), 1.68 (m, 2H), 1.32 (m, 10H), 0.96 (m, 15H).

EXAMPLE 2

4 g (22 mmol) of hydroxymethylenecamphor were reacted with 4.29 g (22 mmol) of butyl o-aminobenzoate by the general method to result in 4.9 g of a compound of the formula:

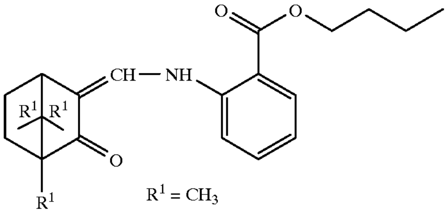

$R^1 = CH_3$

UV($CH_3OH$): $\lambda_{max}$=358 nm, $E_1^1$=802

IR: v=3274, 2943, 1687, 1622 (s), 1602, 1592, 1272, 1246, 1156 $cm^{-1}$.

$^1$H-NMR ($CDCl_3$): δ=10.13 (d, 1H, J=16.2 Hz), 7.98 (d, 1H, J=6.9 Hz), 7.68 (d, 1H, J=16.2 Hz), 7.49 (t, 1H, J=7.2 Hz), 7.21 (d, 1H, J 6.9 Hz), 6.87 (d, 1H, J=7.2 Hz), 4.37 (t, 2H, J=8.1 Hz), 2.81 (m, 1H), 2.11 (m, 1H), 1.4–1.6 (m, 9H), 0.99 (m, 10H).

EXAMPLE 3

The compounds 3.1 to 3.15 stated in Tab. 1 were prepared as in Examples 1 and 2

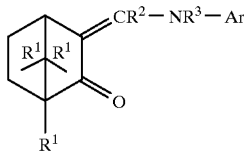

TABLE 1

| Compound | $R^1$ | $R^2$ | $R^3$ | Ar |
|---|---|---|---|---|
| 3.1 | $CH_3$ | H | H | 4-$CH_3$O—Ph |
| 3.2 | $CH_3$ | H | H | 2,4-Di-$CH_3$O—Ph |
| 3.3 | $CH_3$ | $CH_3$ | H | 4-$CH_3$O—Ph |
| 3.4 | $CH_3$ | $CH_3$ | $CH_3$ | 4-$CH_3$O—Ph |
| 3.5 | H | H | H | 4-$CH_3$O—Ph |
| 3.6 | $CH_3$ | H | H | 2-($H_2$N—CO)—Ph |
| 3.7 | $CH_3$ | H | H | 4-($H_2$N—CO)—Ph |
| 3.8 | H | H | H | 3-($CH_3$O—CO)—Ph |
| 3.9 | H | H | H | 4-($C_8H_{17}$O—CO)—Ph |
| 3.10 | $CH_3$ | H | H | 4-quinolinyl |
| 3.11 | $CH_3$ | H | H | 2-$CO_2$H—Ph |
| 3.12 | $CH_3$ | H | H | 4-$SO_3$H—Ph |
| 3.13 | $CH_3$ | H | H | 4-$SO_2NH_2$—Ph |
| 3.14 | $CH_3$ | $CH_3$ | H | 2-$CO_2$H—Ph |
| 3.15 | $CH_3$ | $CH_3$ | H | 2-(n$C_4H_9$O—CO)—Ph |

We claim:

1. A method for the protection of skin from ultraviolet radiation which comprises applying to said skin a composition consisting essentially of an arylaminomethylenecamphor derivative of the formula (1)

(1)

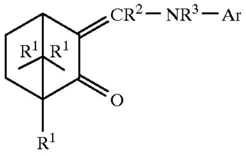

where the C═C double bond is in the Z or E configuration, and l the variables have the following meanings:

$R^1$ H, $CH_3$, $R^2$ H, $C_1$–$C_6$-alkyl, $C_3$–$C_8$-cycloalkyl, $C_2$–$C_6$-alkenyl, $C_3$–$C_8$-cycloalkenyl, cloalkenyl, aryl or substituted aryl, $R^3$ H, $C_1$–$C_6$-alkyl, $C_3$–$C_8$-cycloalkyl, aryl, substituted aryl, $C_1$–$C_6$-alkoxy, $C_1$–$C_8$-acyl, Ar aryl, substituted aryl, hetaryl or substituted hetaryl.

2. A method as claimed in claim 1, wherein the C═C double bond of the arylaminomethylencamphor derivatives of the formula (1) is in the E configuration.

3. An arylaminomethylenecamphor derivative of the formula (1)

(1)

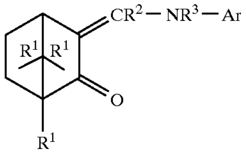

wherein $R^1$ is $Ch_3$, $R^2$═══H and Ar is 2-(alkoxycarbonyl) phenyl.

4. A method as claimed in claim 1, wherein the variables of the arylaminomethylencamphor derivatives of the formula (1) have the following meanings: $R^1$ is $CH_3$, $R^2$=$R^3$=H and Ar is 2-(alkoxycarbonyl)phenyl.

5. A cosmetic composition consisting essentially of an arylaminomethylencamphor derivative of the formula (1) as defined in claim 1.

6. A cosmetic composition as claimed in claim 5, which contains 0.1 to 15% by weight of an arylaminomethylencamphor derivative of the formula (1).

7. An arylaminomethylencamphor derivative as claimed in claim 3, wherein the C=C double bond is in the E configuration.

* * * * *

UNITED STATES PATENT AND TRADEMARK OFFICE

CERTIFICATE OF CORRECTION

PATENT NO.: 5,932,195

DATED: August 3, 1999

INVENTOR(S): DROEGEMUELLER et al.

It is certified that error appears in the above-identified patent and that said Letters Patent is hereby corrected as shown below:

Col. 6, claim 1, line 43, delete "1";
line 46, delete "cloalkenyl".

Col. 6, claim 2, line 52, "derivatives" should be --derivative--.

Col. 6, claim 3, line 66, "$Ch_3$" should be --$CH_3$--; "$R^{2}$" should be --$R^2 = R^3 = H$--.

Col. 7, claim 4, line 2, "derivatives" should be --derivative--.

Signed and Sealed this

Twenty-eighth Day of December, 1999

Attest:

Q. TODD DICKINSON

*Attesting Officer*

*Acting Commissioner of Patents and Trademarks*